United States Patent [19]

Nishimura

[11] Patent Number: 4,757,437
[45] Date of Patent: Jul. 12, 1988

[54] AUTOMATIC SAMPLING APPARATUS

[75] Inventor: Takashi Nishimura, Kyoto, Japan

[73] Assignee: Shimadzu Corporation, Kyoto, Japan

[21] Appl. No.: 883,807

[22] Filed: Jul. 9, 1986

[30] Foreign Application Priority Data

Jul. 13, 1985 [JP] Japan .................. 60-154894

[51] Int. Cl.$^4$ .................. G06F 15/46; G01N 35/06
[52] U.S. Cl. .................. 364/167; 73/863.01;
73/864.25; 364/496; 422/67; 422/100
[58] Field of Search .................. 364/167, 496-500,
364/478, 479; 422/50, 62-67, 75, 99, 100;
436/47, 48, 50, 55; 73/864.24, 864.25, 863.91,
863.92, 863.01

[56] References Cited

U.S. PATENT DOCUMENTS

| | | | |
|---|---|---|---|
| 4,166,483 | 9/1979 | Nordlund | 422/67 X |
| 4,322,216 | 3/1982 | Lillig et al. | 422/67 X |
| 4,422,151 | 12/1983 | Gilson | 73/864.25 X |
| 4,664,885 | 5/1987 | Minekane et al. | 422/67 X |

Primary Examiner—Joseph Ruggiero
Attorney, Agent, or Firm—Armstrong, Nikaido, Marmelstein & Kubovcik

[57] ABSTRACT

An automatic sampling apparatus for individually obtaining samples from a plurality of receptacles in a rectangular array, includes a sample table for supporting a rack containing the array of receptacles, and a sampling device movable in two dimensions above said sample table and receptacles. Further, a control device is provided for receiving positional data from the sampling device in a teaching mode representing the two-dimensional position of the sampling device above the sample table, and for calculating the pitch spacing between receptacles in a single row, and row spacing between adjacent rows of receptacles, wherein the pitch spacing is calculated by arithmetic division of the length of one row by the number of receptacles in a row minus one, and the row spacing is calculated by arithmetic division of the distance between farthest rows by the number of rows minus one. Additionally, the control device is provided for controlling the sample device to individually obtain samples in a stepping manner from the receptacles based on the calculated pitch and row spacings. An operation panel, operatively coupled with the control device, has input keys to position the sampling device for the teaching mode by an operator.

4 Claims, 3 Drawing Sheets

AUTOMATIC SAMPLING APPARATUS

FIELD OF THE INVENTION

This invention relates to an automatic apparatus for individually sampling multiple samples contained in an array of receptacles. In particular, this relates to an automatic sampling apparatus for dispensing a large number of liquid samples individually and sequentially to an analytical apparatus.

DESCRIPTION OF THE RELATED ART

An automatic sampling apparatus has been proposed wherein a number of receptacles, for instance, test tubes containing samples are lined up and respective samples are individually extracted in sequence from the receptacles and supplied to an analytical apparatus. Such conventional automatic sampling apparatuses are suited to deal with liquid samples contained in regular test tubes, where the test tubes are compactly arranged. A sampling nozzle disposed above the text tubes travels in steps with the same pitch as a spontaneously formed interval between respective test tubes in order to sequentially extract a sample from each test tube.

The above conventional devices can be employed where outstanding sample receptacles have a uniform, smaller diametric said than an interval pitch derived from the regular test tubes, but it is inflexible and unsuited for use with receptacles having a uniform, larger diameter than the above interval pitch of the regular test tubes. For instance, this problem arises when samples are extracted from breakers for laboratory use. In view of the fact that a conventional sampling apparatus is restricted with respect to usable receptacle size, the instant invention provides an automatic sampling apparatus which is much more flexible with regard to receptacle size.

SUMMARY OF THE INVENTION

The instant invention overcomes the disadvantages described above by employing an electronic controller which stores, in memory, parameters received in a teaching mode, of a generally rectangular array of receptacles, and wherein a number of receptacles in each row in perpendicular directions are input as manual instructions, and in response thereto, a travel pitch or a one unit distance between adjacent receptacles is calculated by the electronic controller. In other words, the electronic controller enables a travel pitch for the samples to be set by inputting data and the travel pitch is then calculated by dividing the length of one row by the number of receptacles in it.

Accordingly, a sampling device in accordance with the instant invention is not restricted in its travel pitch as in the prior art. On the contrary, the sampling device may sequentially travel between receptacles in a row, according to a prescribed pitch length between receptacles. Thus freely chosen receptacles may be used in an optional rack and the travel pitch *is not* determined by measuring the pitch distance between two adjacent receptacles in a group, but *is* determined by dividing the row length in one direction by the number of receptacles in that row, and thereby, an error in the travel pitch will not accumulate with an increased number of receptacles, as in the prior art.

These drawings are presented by way of illustrating specific inventive embodiments. Therefore attached drawings shoud not be construed as limiting the present invention, which will be described below in accordance with the drawings.

DESCRIPTION OF THE PREFERRED EMBODIMENTS

Figure 1:
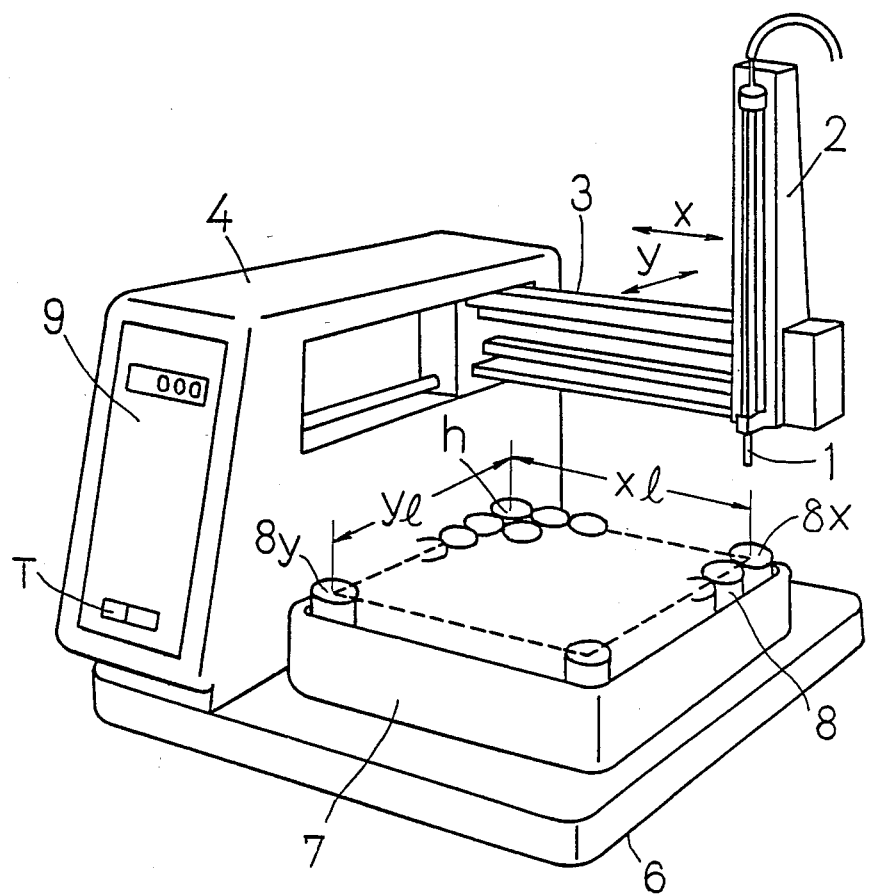
FIG. 1 is a perspective view of an embodiment of the present invention.

FIG. 1 is a perspective drawing of an embodiment of the instant invention. A sampling means 1 is actually a pipetter to suck up or to extract liquid samples and is adapted to effect up and down motions along a vertical guide 2. The vertical guide 2 is moved right and left along a horizontal arm 3 as also shown in FIG. 1 (the X direction). Horizontal arm 3 moves near and far (the Y direction) along a level guide mounted on base 4. Therefore, a sampling device comprises means for moving a sampling means up and down and also in a two-dimensional planar area, for instance, represented by a cartesian coordinate system with directions X and Y.

A sample table 6 defines a part of the apparatus base and a rack 7, not a part of the apparatus, is manually positioned on the sample table 6. Sample receptacles 8 are placed or arrayed thereon. This rack 7 may be freely chosen and accepted so far as it is a square or rectangle having dimensions within the maximum travel distance of the pipetter in the X and Y directions.

An operation panel 9 is elevated on the front of the apparatus and is provided with keys, described below, for inputting data necessary to define sampling behaviors. Behind the panel 9 or in the interior of the body 4, electronic control means include a control device to perform a series of operations as shown in FIG. 3. The control means will be further described in relation to the descriptions of FIGS. 2 and 3, below.

Input keys on panel 9 are used to input necessary data or instructions to the sampling apparatus. After connected the apparatus to a source of electrical power, depressing a TEACHING key, near the bottom of operation panel 9, will set the apparatus in the teaching mode. In the teaching mode, the center h of a receptacle lying at a corner of the array of receptacles, as in FIG. 1, is considered as an origin point (eye determination is permitted). Pipetter 1 is set at the origin point and therefrom is moved along the row in the X direction to the center of a receptacle 8x lying at the right most corner position. By this movement, the control device in the apparatus is instructed to store a travel length xl of the pipetter as location data in the X direction The number of receptacles in the above row in the X-direction is counted and that number is input into the input keys. The control device then calculates the pitch length by dividing whole travel length xl, from the origin to 8x, by the number of receptacles in the above row minus one, so that a travel pitch is determined for the pipeletter 1 to make in the X direction. In the X-direction, the distance beween adjacent receptacles is the pitch spacing.

In the Y direction, as with the X-direction, pipetter 1 is moved from the origin point h to the center of receptacles 8y (perpendicular to the row of receptacles in the X-direction) positioned at the furthest corner position of a row in the Y-direction. The number of the receptacles in the Y-direction is then input to the control device which computes a step length in the Y-direction. For purposes of this disclosure, the step length (or pitch length) in the Y-direction will be referred to as the row spacing.

When the rack 7 is placed on table 6, it is not necessary to accurately orient one side of the rack to be parallel with the X-direction. For example, where a row of the receptacles in the X-direction incudes a Y-component in addition to an inherent X-component (in other words, where location data with the pipetter contain not only one directional component, but also another directional component) no difficulty will result, because one pitch length in either direction is determined by division in view of coordinate components of X and Y with use of respective number of receptacles. In an extreme case a rack may be oriented at an angle of 45 degrees with respect to X and Y directions which represent a coordinate basis to define locations on the table 6. Of course, in such a situation, the pitch spacing and row spacing are not strictly in the X or Y directions respectively.

Figure 2:
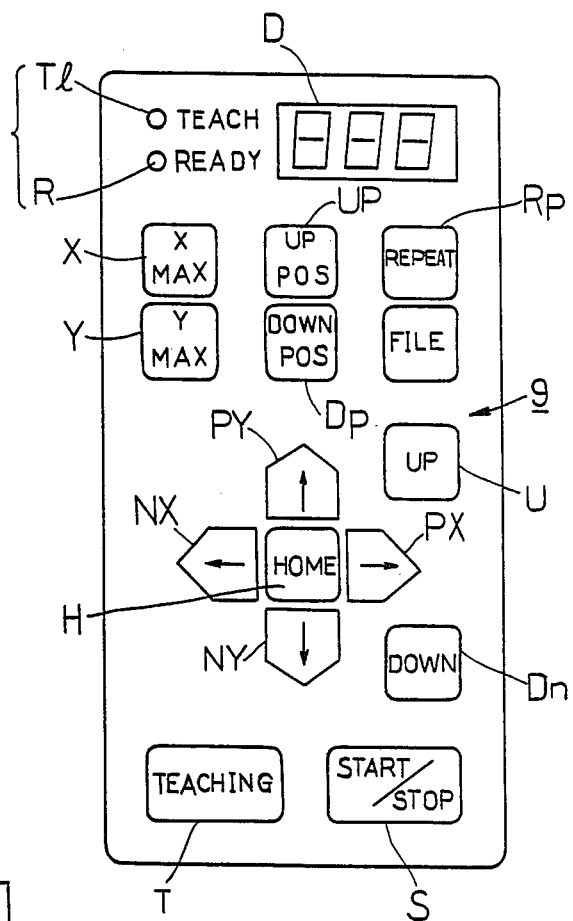
FIG. 2 is a front elevation view of an operation panel mounted in the embodiment of FIG. 1.
Figure 3:
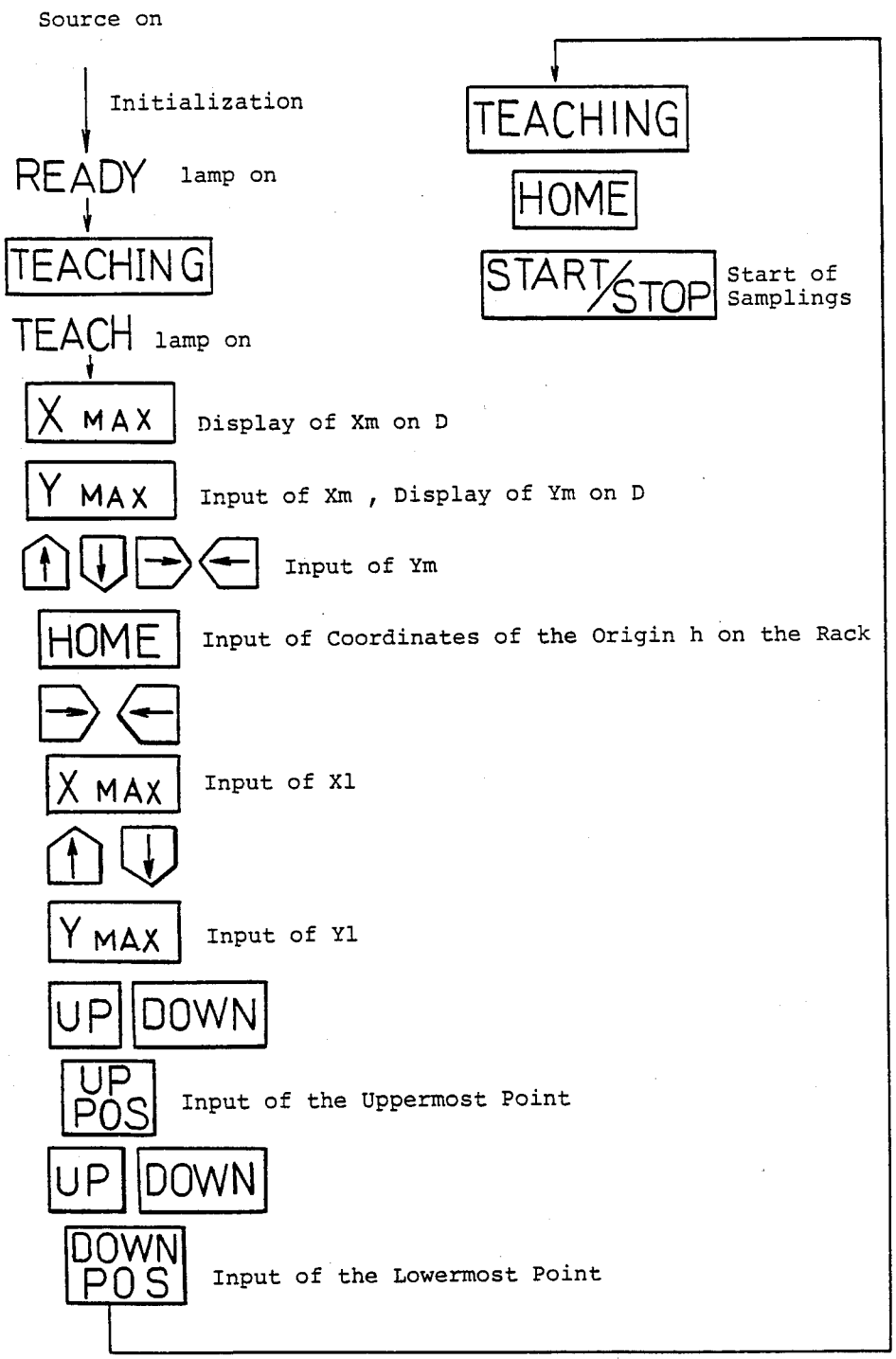
FIG. 3 is a sequential flow chart to show panel operations with use of input keys.

FIG. 2 illustrates the operation panel mounted in the same embodiment. FIG. 3 is a sequential flow chart for input key operations on the panel. Below, a series of the key operations and actions of the apparatus will be noted according to FIGS. 2 and 3. Further, the power switch is turned on so that the electrical source starts initial actions and thereafter the apparatus reaches a standby status. In this state a READY lamp R of the display is lit. In initial actions, the pipetter 1 is positioned at the origin point h of the apparatus, and is also disposed at the uppermost point as to up and down motions.

The depressing of key S for START/STOP in the standby status initiates sampling actions. An essential problem is data input operations for subsequent sampling actions. To accomplish this, TEACHING key T must be depressed. Thus, the READY lamp R is turned OFF and the TEACHING lamp T1 turns ON. Then, the number of receptacles in a row in the X-direction on rack 7 is manually manual input by depressing an X max displaying key X for the number of receptacles in the X-direction, because one depression causes a display of 1 on a numeral display window D. According to the rule of one increment for one depression, a desired number is obtained by repeated depressions and then likewise the number of receptacles in the direction Y on the rack 7 (or the number of rows) is manually input by a corresponding number of depressions of a Y max displaying key Y. A depression of key Y changes a numeral display on the window D from Xm which is transmitted to the control device as input data Xm and simultaneously the display window is changed to indicate the number of depressions of the key Y.

Then, the depressing of another key after a desired numeral setting is input using the key Y, the numeral setting Ym is input to the control device. In the above case, if a key PX arrow-oriented in x direction is assumed to be depressed, as an example another key, pipetter 1 moves in the plus X direction, or to right in FIG. 1, while the key PX remains depressed. Likewise, depressing the NX key makes the pipetter move in the minus X direction. Further, depressing the PY key makes the pipetter move in the plus Y direction and the depression of the NY key makes the pipetter move in the minus Y direction. These keys are first used for positioning pipetter 1 at the origin point (the center of receptacle h in FIG. 1) on the rack. Then a HOME key H is depressed, which acts to input X, Y coordinates of the origin point h on the rack 7 to the control device. Then, the pipetter 1 is moved by the operation of the PX key, for instance, in the x direction up to the center of furthest receptacle 8x in the FIG. 1 and the HOME key H is pushed. Thus, coordinate data of the center of the receptacle 8x is input to the control device. Likewise, coordinate data for receptacle center 8y is input to the control device by similar operations. The control device then calculates the two distances X1 and Y1 as shown in FIG. 1, from the coordinate data of the rack origin point h, 8x and 8y. The control device further calculates the pitch travel distances in both the X and Y-directions for one receptacle allotment. In other words, the pitch spacing in the X-direction is calculated and the row spacing in the Y-direction is calculated. With reference to the previously input data Xm and Ym to the control device, the pitch spacing and row spacing are determined as follows:

pitch spacing = $X1/(Xm-1)$, row spacing = $Y1/(Ym-1)$.

Next, an UP key designated by U and a DOWN key designated by Dn are used to operate the pipetter 1 in up and down motions, by which up and down positions of the pipepetter are set. In sampling actions, the pipetter comes down to the down position to extract a sample and comes up to the up position to travel to the next receptacle. Specific up and down positions may be determined by depressing the "UP position key" designated by UP while the pipetter is held at a higher position, and by pushing a "DOWN position key" designated by DP while the pipetter is held at a lower position.

After inputting the necessary data as noted above, depressing the TEACHING key again returns the apparatus to the standby status. At this point, depressing the HOME key moves the pipetter 1 to the rack origin point (the center of the receptacle h) while staying at the higher position. Then, depressing the START/STOP key S initiates the series of the automatic sampling operations and when finished the appartus returns automatically to the standby status.

On the operation panel 9, a REPEAT key RP is provided in addition to other keys as noted above. This key instructs the control device how many times the sampling should be repeated with respective receptacles when, of necessity, samplings must be done a plurality of times prior to being supplied to the next analyzer. Further depressing the RP key renders a numeral in the numeral displaying window. Therefore, if two times of sampling at respective receptacles is desired, depressing the RP key two times renders a display of 2 and depressing the START/STOP key S will accomplish sampling two times at respective receptacles.

Figure 4:
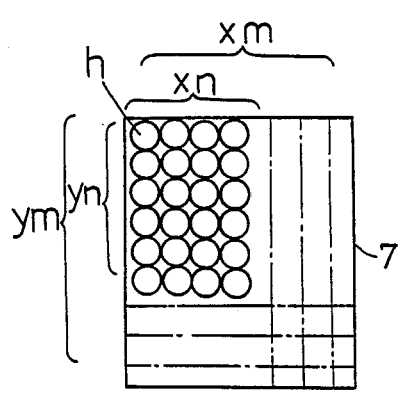
FIG. 4 is a plan view showing an example or receptacles arrayed in a rack.

Further, when rack 7 is not full of receptacles as shown in FIG. 4 and empty sampling operations at absent positions is considered to be a loss of time, after setting Xm, Ym in the TEACHING mode, the same Xm and Ym keys may be operated to input Xm and Ym at the time of standby status, and depressing the START/STOP key thereafter enables the sampling device or pipetter to be appropriately positioned to properly sample the contents of the receptacles in the range of Xn and Yn.

When racks having the same shape are used in sequence, repeated data input processing is not necessary, but it is necessary to place the rack at the same position as a previous rack. Further is required, new Xn, Yn and repeating instructions are input followed by depressing the STAR/STOP key S, the sampling operations will be performed with the same interval data as in a previous sampling. In FIG. 1, setting marks are not shown for placing the rack on the sample table 6 to mark the same position, but these are marked behind the rack 7 in the illustrated embodiment, so that placing the rack in contact with marks on the side wall of the body 4 enables the rack to automatically be located at the same position, every time.

The above described invention enables a travel pitch of a sampling device to be determined at will, thereby enabling receptacles of different sizes to be used by the automatic sampler at different times. Further, as shown in the disclosed embodiment, setting one travel pitch is determined by inputting the whole row length and the number of receptacles therein and by arithmetic calculation thereof instead of inputting data of receptacle size or pitch of rows of receptacles. The instant invention is free from accumulation errors between a true pitch length and a set pitch length, which errors will lead to large mis-match or mis-alignment in locating the sampling means from an aimed receptacle lying at a far position in a row. Such disadvantages are common in a conventional, direct input method of pitch data as noted above.

It should be noted that those skilled in the art understand that the descriptions above are directed to preferred embodiments and that various alterations or modifications may be contemplated without departing from the spirit and scope of the invention as set forth in the following Claims.

I claim:

1. An automatic sampling apparatus, comprising:
  a sampling device for sampling a plurality of sample receptacles arranged in a least one row, wherein said sampling device samples in a stepping manner from one receptacle to another based upon a calculated pitch spacing; and
  a control means operatively controlling said sampling device for calculating said pitch spacing in response to a teaching input by arithmetic division of the length of said one row of sample receptacles by the number of receptacles in said row minus one.

2. An automatic sampling apparatus for individually obtaining samples from a plurality of receptacles in a rectangular array, comprising:
  a sample table for supporting a rack containing the array of receptacles;
  a sampling device movable in two dimensions above said sample table and receptacles;
  a control means for receiving positional data from said sampling device in a teaching mode represently the two-dimensional position of said sampling device above said sample table, and for calculating the pitch spacing between receptacles in a single row, and row spacing between adjacent rows of receptacles, wherein said pitch spacing is calculated by arithmetic division of the length of one row by the number of receptacles in a row minus one, and said row spacing is calculated by arithmetic division of the distance between farthest rows by the number of rows minus one, and further for controlling said sample device to individually obtain samples in a stepping manner from said receptacles based on said calculated pitch and row spacings; and
  an operation panel, operatively coupled with said control means, and having input keys to position said sampling device for said teaching mode of an operator.

3. The automatic sampling apparatus of claim 2, wherein in said teaching mode, in response to operator control of said operator panel, said control means centers said sampling device directly over a receptacle positioned at a corner of said receptacle array to establish an origin point, and wherein said length of one row is determined by centering said sampling device directly above the farthest most receptacle of the row of said origin point, and further wherein said distance between the farthest rows is determined by centering said sampling device over a receptacle in the farthest row from said origin point, perpendicular with respect to said origin point and its row.

4. The automatic sampling apparatus of claim 2, wherein said receptacle array is aligned perpendicularly with a movement axis of said sampling device.

* * * * *